United States Patent
Gronovich (10) Patent No.: US 10,716,655 B2
(45) Date of Patent: Jul. 21, 2020

(54) NECK LIFT SLING

(71) Applicant: SHAARE ZEDEK SCIENTIFIC LTD., Jerusalem (IL)

(72) Inventor: Yoav Gronovich, Jerusalem (IL)

(73) Assignee: SHAARE ZEDEK SCIENTIFIC LTD., Jerusalem (IL)

( * ) Notice: Subject to any disclaimer, the term of this patent is extended or adjusted under 35 U.S.C. 154(b) by 57 days.

(21) Appl. No.: 16/073,943

(22) PCT Filed: Feb. 2, 2017

(86) PCT No.: PCT/IL2017/050131
§ 371 (c)(1),
(2) Date: Jul. 30, 2018

(87) PCT Pub. No.: WO2017/134670
PCT Pub. Date: Aug. 10, 2017

(65) Prior Publication Data
US 2019/0038391 A1 Feb. 7, 2019

Related U.S. Application Data (60) Provisional application No. 62/290,562, filed on Feb. 3, 2016.

(51) Int. Cl.
*A61F 2/00* (2006.01)
*A61L 27/58* (2006.01)

(52) U.S. Cl.
CPC .......... *A61F 2/0059* (2013.01); *A61F 2/0063* (2013.01); *A61L 27/58* (2013.01);
(Continued)

(58) Field of Classification Search
CPC .... A61F 2/0045; A61F 2/0059; A61F 2/0063; A61F 2230/0054; A61B 2017/00792
See application file for complete search history.

(56) References Cited

U.S. PATENT DOCUMENTS

| 3,021,845 A | 2/1962 | Smith |
| 5,217,494 A | 6/1993 | Coggins et al. |

(Continued)

FOREIGN PATENT DOCUMENTS

| CN | 204655198 U | 9/2015 |
| FR | 2682284 A1 | 4/1993 |

(Continued)

OTHER PUBLICATIONS

International Search Report PCT/IL2017/050131 Completed May 17, 2017: dated May 18, 2017 4 pages.
(Continued)

*Primary Examiner* — Brian A Dukert
*Assistant Examiner* — Amanda M Barkan
(74) *Attorney, Agent, or Firm* — The Roy Gross Law Firm, LLC; Roy Gross (57) ABSTRACT

A subcutaneous sling for neck lift surgery. The sling comprises a sling body, shaped to fit in a submental triangle of a patient undergoing neck lift surgery, comprising a narrow anterior edge for anchoring near the chin of the patient. The sling comprises two lateral sling extensions, each coupled to a respective side edge of two sides of the sling body, each projecting away from the center of the sling body in a posterior lateral orientation of between 45 and 90 degrees from the anterior-posterior axis, and curved slightly towards the narrow anterior edge to fit the submandibular triangle and extend to near each ear of the patient. The sling body is at least 4 centimeters long in the anterior-posterior dimension, and the ends of the two lateral sling extensions are at least 14 centimeters distant from each other.

10 Claims, 4 Drawing Sheets

(52) U.S. Cl.
CPC ............... *A61F 2210/0004* (2013.01); *A61F 2230/0054* (2013.01)

(56) References Cited

U.S. PATENT DOCUMENTS

| | | |
|---|---|---|
| 5,584,884 A | 12/1996 | Pignataro |
| 6,402,585 B1 | 6/2002 | Gatto et al. |
| 6,485,503 B2 | 11/2002 | Jacobs et al. |
| 6,599,318 B1 | 7/2003 | Gabbay |
| 7,361,138 B2 | 4/2008 | Wagner et al. |
| 7,824,326 B2 | 11/2010 | Wagner et al. |
| 2002/0029011 A1* | 3/2002 | Dyer ............... A61L 31/125 602/41 |
| 2009/0062600 A1* | 3/2009 | Hallum ............ A61F 2/0045 600/37 |
| 2009/0082791 A1 | 3/2009 | Schroeder et al. |
| 2010/0204791 A1* | 8/2010 | Shfaram .......... A61B 17/0401 623/8 |
| 2010/0217388 A1 | 8/2010 | Cohen et al. |
| 2012/0150204 A1 | 6/2012 | Mortarino et al. |
| 2013/0211192 A1* | 8/2013 | Moschel .......... A61F 2/0045 600/37 |
| 2013/0253645 A1 | 9/2013 | Kerr et al. |
| 2014/0257032 A1* | 9/2014 | Hacker ........... A61B 17/06109 600/37 |
| 2015/0012019 A1 | 1/2015 | Huelskamp et al. |
| 2015/0223928 A1* | 8/2015 | Limem .............. A61F 2/12 623/8 |

FOREIGN PATENT DOCUMENTS

| | | |
|---|---|---|
| RU | 2454959 C1 | 7/2012 |
| WO | 2006133478 A1 | 12/2006 |
| WO | 2009050706 A2 | 4/2009 |

OTHER PUBLICATIONS

International Search Report PCT/IL2017/050131 dated May 18, 2017 4 pages.

* cited by examiner

NECK LIFT SLING

CROSS-REFERENCE TO RELATED APPLICATIONS

This application is a National Phase of PCT Patent Application No. PCT/IL2017/050131 having International filing date of Feb. 2, 2017, which claims the benefit of priority of U.S. Patent Application No. 62/290,562, filed on Feb. 3, 2016 and titled "Neck Lift Sling". The contents of the above applications are all incorporated by reference as if fully set forth herein in their entirety.

FIELD OF THE INVENTION

The invention relates to the field of neck lift surgery.

BACKGROUND

In plastic surgery, a neck lift, or lower rhytidectomy, is a surgical procedure that improves visible signs of aging in the jawline and neck. A neck lift may remove excess fat and skin in the lower face that creates jowls, remove fatty deposits under the chin, tighten loose neck skin, adjust muscle banding in the neck, for example that create abnormal contours, and/or the like. Factors that cause the need for a neck lift may include heredity, gravity, environmental conditions, stress, and/or the like. These factors may cause excess wrinkling of the neck skin, such as referred to colloquially as "turkey wattle" or a double chin, and impair jowl lines.

Other procedures related to lower rhytidectomy are cervicoplasty and platysmaplasty, which are correction of submental ptosis sometimes necessary to reverse the effects of aging. Cervicoplasty and platysmaplasty may be performed together with facial rhytidectomy, when surgeons may need to address the cervical region.

Originating from the pectoralis major muscle fascia, the platysma is a layer of muscle that has multiple insertions. Moving anterior to posterior, the muscle is anchored to the mentum and the inferior mandibular border and meets the orbicularis oris laterally and then the depressor anguli oris. Platysmal meshing with the depressor anguli oris contributes to the superficial muscular aponeurotic system (SMAS), highlighting its importance when attempting to reverse facial aging.

A neck lift may be performed by a horizontal submental incision for lipectomy, with excision or plication of hypertrophic anterior platysmal bands, and wide subcutaneous cervical dissection. This may correct fasciocutaneous ligaments extending from the dermis to the facial fascia, and osseocutaneous ligaments extend from the dermis to the periosteum.

Adipose tissue may comprise subcutaneous and subplatysmal fat tissue. Increased amounts of subcutaneous fat may be observed with weight gain, aging, lipodystrophies, and/or the like. Subplatysmal fat is far more vascular and fibrous than subcutaneous fat and is visualized after incising the platysma muscle. This difference may result in reduced efficacy of liposuction of subplatysmal fat.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with some embodiments, a subcutaneous sling for neck lift surgery. The sling comprises a sling body, shaped to fit in a submental triangle of a patient undergoing neck lift surgery, comprising a narrow anterior edge for anchoring near the chin of the patient. The sling comprises two lateral sling extensions, each coupled to a respective side edge of two sides of the sling body, each projecting away from the center of the sling body in a posterior lateral orientation of between 45 and 90 degrees from the anterior-posterior axis, and curved slightly towards the narrow anterior edge to fit the submandibular triangle and extend to near each ear of the patient. The sling body is at least 4 centimeters long in the anterior-posterior dimension, and the ends of the two lateral sling extensions are at least 14 centimeters distant from each other.

Optionally, the sling body and two lateral sling extensions are fabricated from one or more biocompatible materials.

Optionally, the sling body and two lateral sling extensions are fabricated from one or more bio-absorbable materials.

Optionally, the sling body and two lateral sling extensions are fabricated from one or more materials from the group consisting of a plastic, a metal, a biological tissue, and combinations thereof.

Optionally, the sling body and two lateral sling extensions are fabricated from one or more bio-absorbable plastic materials from the group consisting of a biodegradable plastic, biodegradable synthetic polymer. biodegradable thermoplastic polymer, biodegradable polyester, biodegradable copolymer, biocompatible plastic, and composites thereof.

Optionally, the sling body and two lateral sling extensions are fabricated from one or more bio-absorbable plastic materials from the group consisting of an absorbable polyglactin 910, polydioxanone, polyglycolic-acid, polylactic acid, poly(lactic-co-glycolic acid), polycaprolactone, polyglycolide, polydioxanone, and polyhydroxybutyrate.

Optionally, the sling body and two lateral sling extensions are fabricated from one or more implant-grade biocompatible materials from the group consisting of a polyvinyl chloride, polyethylene, polyether ether ketone, polycarbonate, polyetherimide, polysulfone, polypropylene, polyurethane, 316L stainless steel, CoCrMo, Ti6Al4V, Ti6Al7Nb, TiNi, and TiMo.

Optionally, the sling body and two lateral sling extensions are fabricated from one or more materials from the group consisting of an allograft, an isograft, a homograft, and a xenograft.

Optionally, the sling body and two lateral sling extensions are fabricated from one or more material types from the group consisting of a flexible mesh, a flexible grid, a flexible plate, and a flexible sheet.

Optionally, the subcutaneous sling further comprises an interface region between the sling body and each of the two lateral sling extensions, wherein each interface region is one or more from the group consisting of a material more flexible than the sling body, a material thinner than the sling body, and a hinge.

Optionally, the subcutaneous sling further comprises one or more apertures near the middle of the narrow anterior edge for anchoring the sling body near the chin of the patient.

Optionally, the subcutaneous sling further comprises one or more apertures near a distal end of each of the two lateral sling extensions for anchoring each end near each respective ear of the patient.

There is provided, in accordance with some embodiments, a medical method for anchoring a subcutaneous sling in neck lift surgery. The method comprises the action of making incisions near each ear of a patient along a posterior edge of the tragus down through the lobule and posteriorly at the retroauricular sulcus through the hairline, and near a chin of the patient parallel to the mental crease line and five millimeters posterior to the crease line, wherein the incision cut near the chin has a length of 4 centimeters. The method comprises the action of creating a subcutaneous pocket between the incisions. The method comprises the action of inserting a sling into the subcutaneous pocket, wherein the sling comprises a sling body with a front edge, and two extension starting at each side of the sling and extending posteriorly and laterally from the center of the sling body. The method comprises the action of unfolding the sling. The method comprises the action of anchoring the ends of the two extensions near the subcutaneous connective tissue near the ear, and the front edge of the sling to the subcutaneous tissue near the chin.

There is provided, in accordance with some embodiments, a surgical device for inserting a subcutaneous sling in neck lift surgery. The surgical device comprises two handles. The surgical device comprises an aperture for receiving a folded subcutaneous sling. The surgical device comprises a lever for ejecting the folded subcutaneous sling when the surgical device is removed from a subcutaneous pocket.

There is provided, in accordance with some embodiments, a surgical device for folding a subcutaneous sling in neck lift surgery. The surgical device comprises an aperture for receiving a subcutaneous sling. The surgical device comprises a lever for folding the subcutaneous sling and inserting the folded sling into a second surgical device.

There is provided, in accordance with some embodiments, a surgical device for anchoring a subcutaneous sling in neck lift surgery. The surgical device comprises a handle. The surgical device comprises a tensioning lever for grasping an edge of a subcutaneous sling positioned in a subcutaneous pocket. The surgical device comprises a suturing lever for anchoring the subcutaneous sling to a region of connecting tissue.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

According to some embodiments of the invention, there are provided devices and methods for neck lift surgery, such as lower rhytidectomy, to treat loose neck skin. An implantable sling is provided that is shaped to cover at least the submental and/or submandibular triangle, and is fabricated from a biocompatible material, such as a permanent or absorbable biocompatible material, that is positioned subcutaneously, and anchored subcutaneously to the connective tissue at the chin and near the ears. For example, the submental and/or submandibular portion of the sling, such as the sling body, is sized to fit in an anterior-posterior direction from the chin to the cricoid cartilage. For example, the sling is trapezoid or triangle-shaped with edges at least 4 centimeters long and rounded corners. The sling may have a central sling body for supporting the tissue, and extensions from the sling body towards the posterior auricles or the ears to provide anchoring support for the sling body. For example, the sling is sized to fit in the lateral direction from behind the left lobule to behind the right lobule.

For example, the extensions extend from the bode rearward at an angle. For example, the extensions extend from the bode rearward at a 45 degree angle, a 60 degree angle, a 75 degree angle, a 90 degree angle, or the like. For example, the extensions extend from the body rearward at an angle of between 45 and 90 degrees. For example, the extensions extend from the bode rearward at an angle of between 30 and 105 degrees.

Optionally, sling extensions extend from the lateral edges of the sling body in the posterior direction, such as away from the sling body center, to allow anchoring to the connective tissue near the ears.

Optionally, the sling is prefabricated in multiple sizes to fit different patients. For example, the TABLE 1 lists possible prefabricated sizes in centimeters.

TABLE 1

| Size Name | Anterior-Posterior Size | Lateral Size |
| --- | --- | --- |
| XS | 4 | 14 |
| S | 5 | 17 |
| M | 6 | 20 |
| L | 7 | 25 |
| XL | 8 | 30 |
| XXL | 9 | 35 |

Optionally, the sling is partially prefabricated and partially customized to the patient geometry prior to surgery. For example, the sling may be custom made prior to the surgery, such as using a prototyping printer, a partially cut blank sling, and/or the like.

Optionally, the sling is anchored using prefabricated holes in the sling and/or extensions near the corners of the triangle and/or the ends of the extensions.

Optionally, the sling includes extensions that are cut to a length that fits a specific patient, and holes are punched at the ends of the cut extensions.

The sling may be described by three major parts. A sling body that is shaped to support the connective tissue of the submental and/or submandibular triangles, and two extensions, extending posteriorly and laterally to the left and right of the sling body, to anchor the sling body near the ears. For example, the extensions extend to below the ears and are anchored to the subcutaneous connective tissue near the ear. For example, the sling is an isosceles or equilateral triangle with rounded corners and edges at least 4 centimeters long. For example, the edges have contours to match the structure of the submental and/or submandibular triangles.

Reference is now made to FIG. 1, FIG. 2, FIG. 3, FIG. 4, and FIG. 5, which are schematic illustrations of a submandibular sling of a first, second, third, fourth and fifth respective shape for neck lift surgery, according to some embodiments of the invention. As some components of FIG. 1, FIG. 2, FIG. 3, FIG. 4, and FIG. 5 are similar, the first digit of the reference number refers to the respective of drawing of FIG. 1, FIG. 2, FIG. 3, FIG. 4, and FIG. 5, and the following description will use the reference numbers of FIG. 1 for brevity. For example, is it understood that the body of a sling may be referred to as 101, but in FIG. 4 this would correspond to 401. Sling 100 comprises a sling body 101, and two extensions 102 and 103 to the lateral left and right sides of the sling body fabricated from a single piece of material. The anterior edge of the sling body 101 comprises one or more anterior middle holes 106 for anchoring sling 100 to the subcutaneous connective tissue near the chin, and each extension comprises one or more lateral holes as at 104 and 105 respectively for anchoring each extension to the subcutaneous connective tissue near each respective ear. The different shapes as referred to in FIG. 1 FIG. 2, FIG. 3, FIG. 4, and FIG. 5 may be selected based on patient anatomy shape, sling size availability, manufacturing convenience, market branding and/or differentiation, and/or the like.

Optionally, the sling body and sling extensions are separate subunits of the sling. For example, the sling body is a first subunit inserted in a folded mode through an incision at the chin. The sling extensions may be fabricated from a second material, such as a more rigid material, and inserted from the incisions near the ears and coupled to the sling body after insertion. For example, the sling extensions are coupled to the sling body by snaps, adapters, grooves, sutures, adhesive, glue, and the like. For example, the coupling mechanism is fabricated from a bio-absorbable material. Such an embodiment may allow the benefits of a shorter procedure time, a better supported sling body, an improved cosmetic appearance, less need for a postoperative neck support, and the like.

The sling may be anchored to the connective tissue near the chin and ears using sutures, staples, screws, hooks, adhesive, glue, combinations thereof, and/or the like. For example, the sling is sutured to subcutaneous ligaments near the chin and ears. As another example, the sling is stapled to the bones near the chin and ears. As yet another example, the sling is anchored with screws near the ears and sutures near the chin. As yet another example, the sling is anchored with hooks that are located at the edges of the sling, and are exposed when the sling is unfolded and/or unrolled. The hooks may be of the same material as the sling, or a different material, and may be structured to form an array of hooks, analogous to the array of hooks used in hook and loop textile fasteners. The sutures, staples, screws may be made from similar materials as the sling, such as bio-absorbable materials and/or the like, or from different materials, such as biocompatible metals and/or the like. The adhesive or glue may be a biocompatible material. The adhesive or glue may be a bio-absorbable or a permanent material, corresponding to the sling material.

Figure 1:
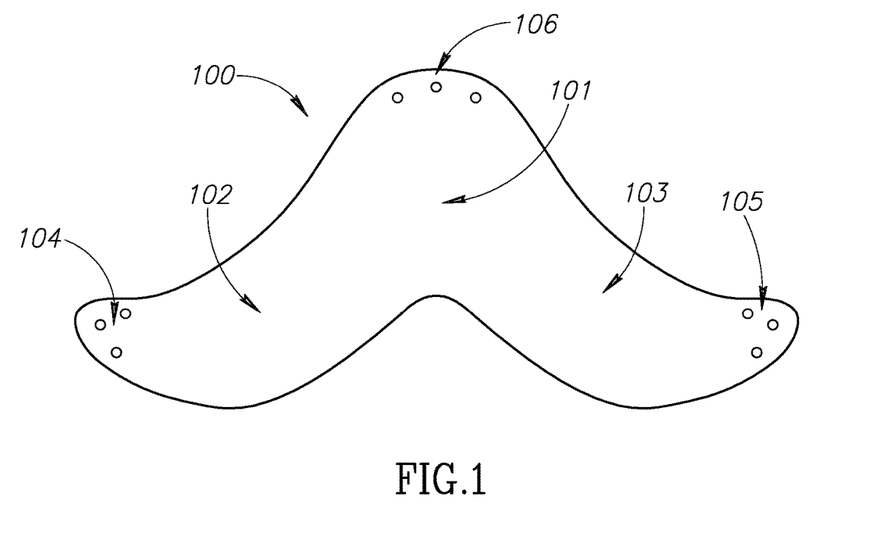
FIG. 1 shows a schematic illustration of a submandibular sling of a first shape for neck lift surgery, according to some embodiments of the invention.
Figure 2:
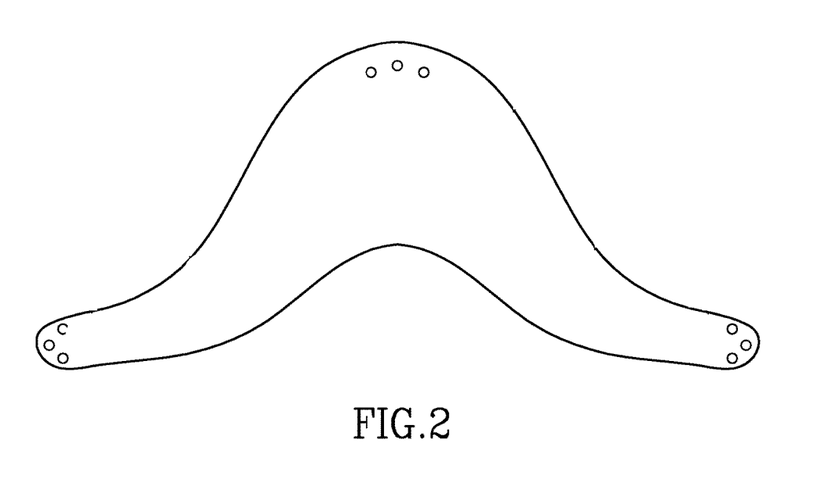
FIG. 2 shows a schematic illustration of a submandibular sling of a second shape for neck lift surgery, according to some embodiments of the invention.
Figure 3:
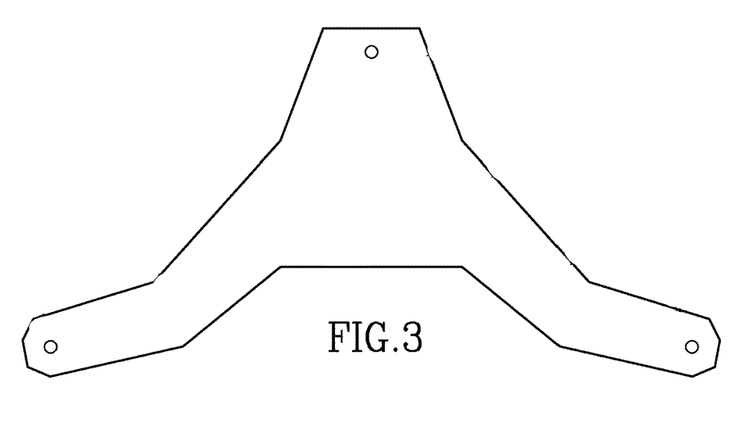
FIG. 3 shows a schematic illustration of a submandibular sling of a third shape for neck lift surgery, according to some embodiments of the invention.
Figure 4:
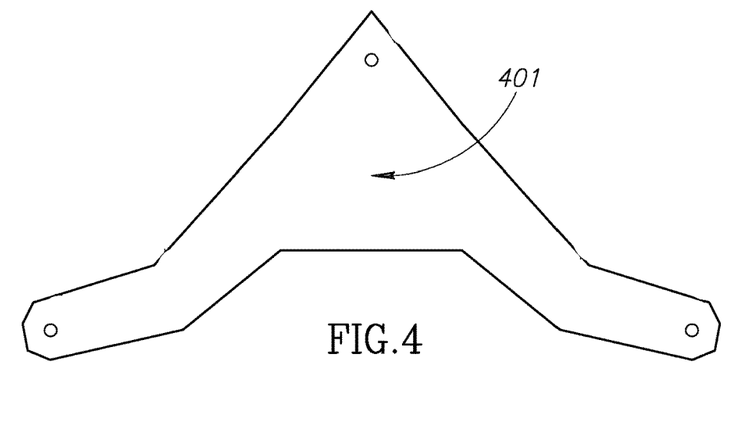
FIG. 4 shows a schematic illustration of a submandibular sling of a fourth shape for neck lift surgery, according to some embodiments of the invention.
Figure 5:
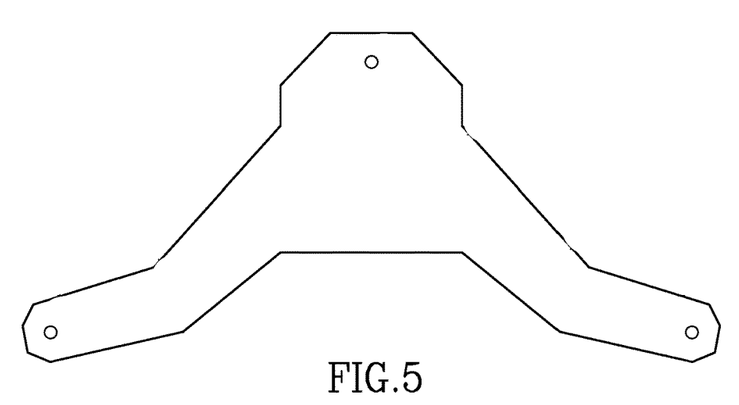
FIG. 5 shows a schematic illustration of a submandibular sling of a fifth shape for neck lift surgery, according to some embodiments of the invention.

Optionally, holes are prefabricated in the corners of sling 100 for anchoring to the chin and subaural connective tissue. For example, three holes are prefabricated in each lateral and medial end of the extensions of sling 100, and at the anterior corner. Each hole may be of 2 millimeter diameter and located 3 millimeters from the edge of sling 100. Optionally, the holes may be between 0.5 and 5 millimeters in diameter and located between 0.2 and 20 millimeters from an edge and/or corner of the sling. The number of holes, their location, and their size may be chosen according to ease of attachment, to the particular anatomy of a subject, for a particular method of attachment, for a particular configuration of components, for a particular shape of sling, and/or the like.

Optionally, holes are custom cut and/or punched in sling 100 for each patient. For example, sling 100 has long extension portions that are cut to fit the patient anatomy and holes are punched in near the cut ends to anchor the submandibular sling body of sling 100.

Sling 100 material may be constructed as a flexible mesh, a flexible grid, a flexible plate, a flexible sheet, and/or the like. Optionally, different regions of sling 100 have different thicknesses and/or material flexibilities to better contour the submandibular triangle, increase patient comfort, allow easier folding and/or insertion, and/or the like. For example, the base of each extension is a more flexible material and/or of thinner material thickness to better fold around the mandibular angle and/or mandibular ramus.

Optionally, the sling structure comprises elastic structural components that assist in opening the sling after insertion to a subcutaneous pocket. The elastic structural components may be permanently elastic, such as a thick elastic backbone, or temporarily elastic, such as an inflatable rib structure. For example, the sling structure contains ribs that support the sling in an open configuration, the sling rib structure is compressed by elastically folding, bending, rolling, and/or the like, inserted into a subcutaneous pocket, and released to elastically change back to the open configuration. For example, the rib structure is made of the same material as the sling but selectively thicker in regions to be elastic. For example, the sling structure comprises integrated inflatable cavities, and after insertion into the subcutaneous pocket, the cavities are inflated and expand the sling to an open configuration.

Biocompatible materials for construction of sling 100 include plastics, metals, biological tissues, composites, and/or the like.

Plastics may include biodegradable plastics, biodegradable synthetic polymers. biodegradable thermoplastic polymers, biodegradable polyesters, biodegradable copolymers, biocompatible plastics.

Specific plastics may be absorbable polyglactin 910, polydioxanone, polyglycolic-acid, polylactic acid, poly(lactic-co-glycolic acid), polycaprolactone, polyglycolide, polydioxanone, polyhydroxybutyrate, and/or the like.

Plastic materials for permanent slings, such as a sling 100 prosthesis, may be implant-grade biocompatible plastics, such as medical grades of polyvinyl chloride, polyethylene, polyether ether ketone, polycarbonate, polyetherimide, polysulfone, polypropylene, polyurethane, and/or the like.

Permanently biocompatible flexible metal mesh may be used from titanium (Ti), stainless steel (SS), alloys thereof, metal alloys, and/or the like. Specific biocompatible metal meshes may be from one or more of the materials: 316L SS, CoCrMo, Ti6Al4V, Ti6Al7Nb, TiNi, TiMo, and/or the like.

Biological tissue used as a submandibular sling may be an autograft, an allograft, an isograft, a homograft, a xenograft, and/or the like. For example, sling 100 is fabricated from the excess skin or the neck. For example, sling 100 is fabricated from dermal tissue grown in vitro. For example, sling 100 is fabricated from biocompatible animal tissue.

Optionally, one or more special surgical devices may be used to insert and position sling 100 subcutaneously. For example, a special purpose surgical device holds sling 100 in a folded mode, inserts sling 100 through a small incision into a subcutaneous pocket, and then spreads sling 100 in place.

Optionally, a surgical device for inserting a subcutaneous sling in neck lift surgery comprises two handles, an aperture for receiving a folded subcutaneous sling, and a lever for ejecting the folded subcutaneous sling when the surgical device is removed from a subcutaneous pocket. Optionally, a surgical device for folding a subcutaneous sling in neck lift surgery comprises an aperture for receiving a subcutaneous sling, and a lever for folding the subcutaneous sling and inserting the folded sling into a second surgical device. Optionally, a surgical device for anchoring a subcutaneous sling in neck lift surgery comprises a handle, a tensioning lever for grasping an edge of a subcutaneous sling positioned in a subcutaneous pocket, and a suturing lever for anchoring the subcutaneous sling to a region of connecting tissue.

Figure 6:
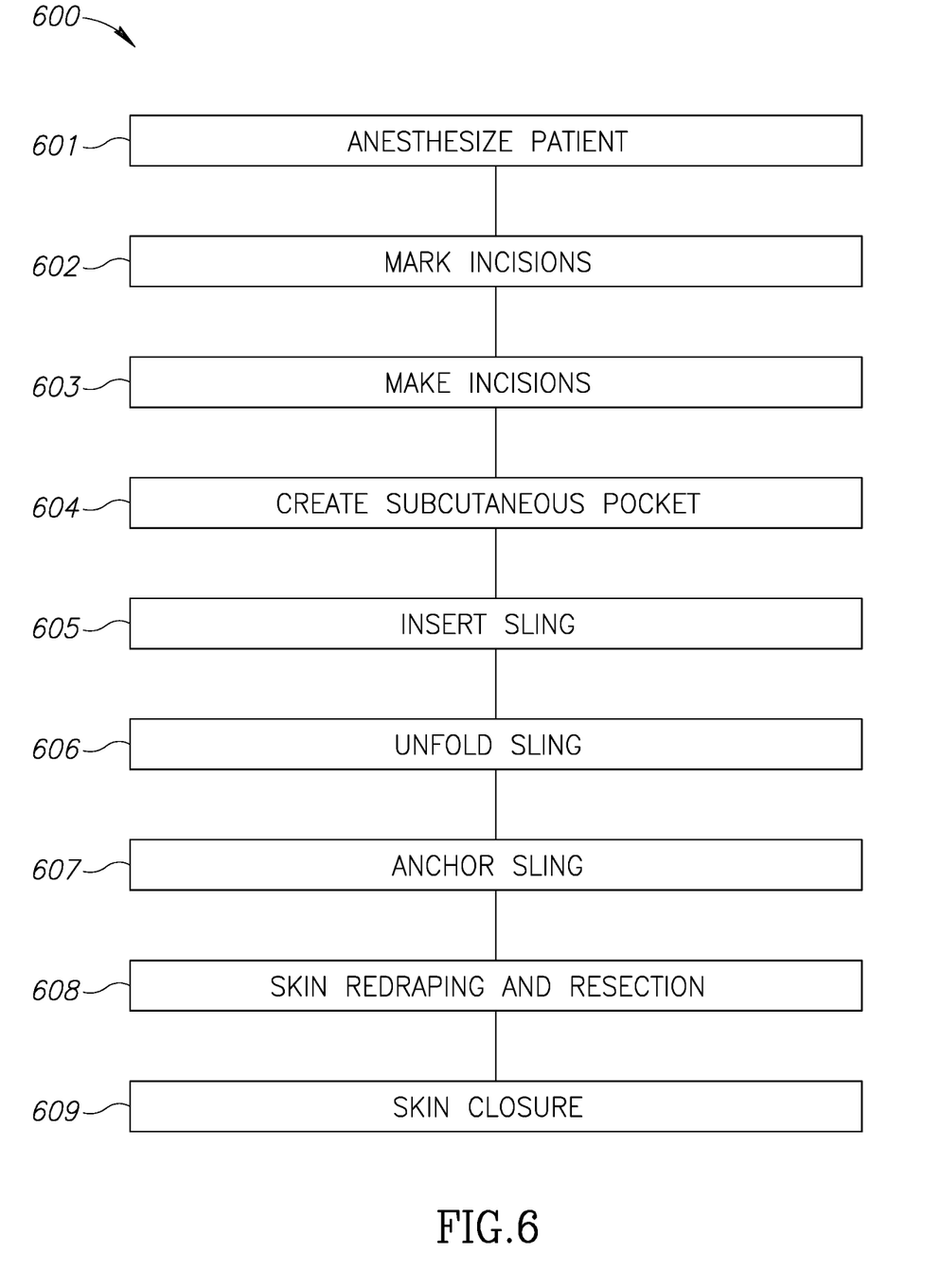
FIG. 6 shows a flowchart of a medical method for neck lift surgery, according to some embodiments of the invention.

Reference is now made to FIG. 6, which is a flowchart of a medical method 600 for neck lift surgery, according to some embodiments of the invention.

A patient is anesthetized 601 and positioned supine on a surgical table. For example, the procedure may be done under local anesthesia, sedation or general anesthesia.

Figure 7A:
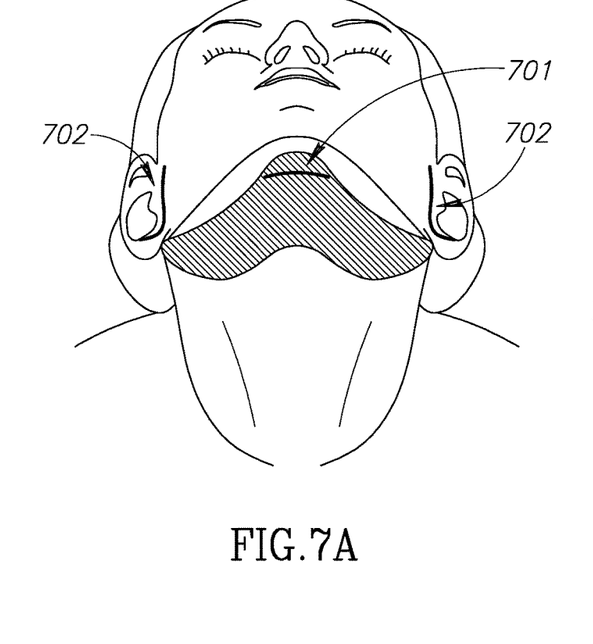
FIG. 7A shows a schematic illustration of a first view of incisions for neck lift sling surgery, according to some embodiments of the invention.
Figure 7B:
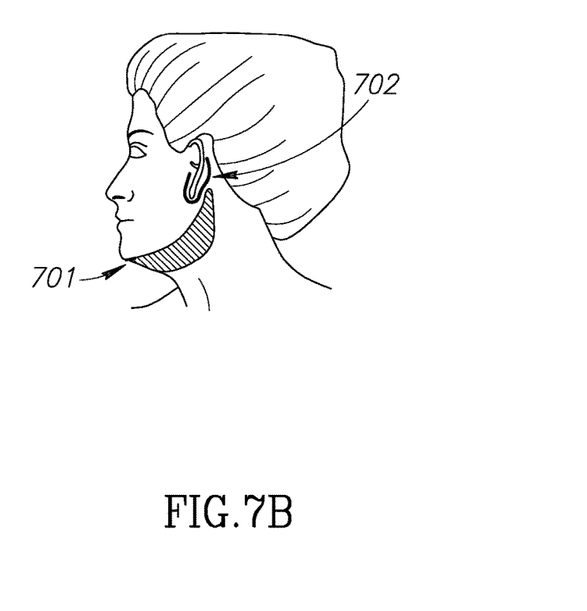
FIG. 7B shows a schematic illustration of a second view of incisions for neck lift sling surgery, according to some embodiments of the invention.

Reference is now made to FIG. 7A and FIG. 7B, which are schematic illustration of views of incisions for neck lift sling surgery, according to some embodiments of the invention. The posterior edge of the tragus 702 may be marked 602 down through the lobule and posteriorly at the retroauricular sulcus through the hairline. Mental crease line 701 may be marked 602 five millimeters posterior to the crease, for a length of 4 centimeters. Optionally, the markings may be located at various locations and of various sizes according to ease of attachment, to the particular anatomy of a subject, for a particular method of attachment, for a particular configuration of components, for a particular shape of sling, and/or the like. For example, the markings may be located between 1 and 25 millimeters posterior to the mental crease for a length of between 1 and 10 centimeters.

Incisions may be cut 603 in the mental crease, then on the distal half of the retroauricular sulcus. In cases of excessive skin redundancy, the incision may be cut preauricularly to the lobule and the edge of the tragus.

To create 604 a subcutaneous pocket, local infiltration and undermining is performed. Local infiltration to the subcutaneous plane may be with NaCl 0.9% 100 cc, epinephrine 1:300,000, and local anesthetics when the procedure is done under local anesthesia. Undermining of the skin may be performed using Gorney scissors in a subcutaneous plane. Most of the dissection may be accomplished by spreading maneuvers of the scissors. The undermining may be performed from the three mentioned incisions: one mental and two retroauricular. In the mental incision, dissection may be performed also anteriorly to the chin for correction of ptosis and creation of space for the edge of sling 100.

After the subcutaneous plane is created, meticulous hemostasis is done under direct vision. Pockets are packed with soaked gauzes, one from each incision, with povidine iodine and sling 100 packaging is opened and sling 100 is prepared for insertion.

Figure 8:
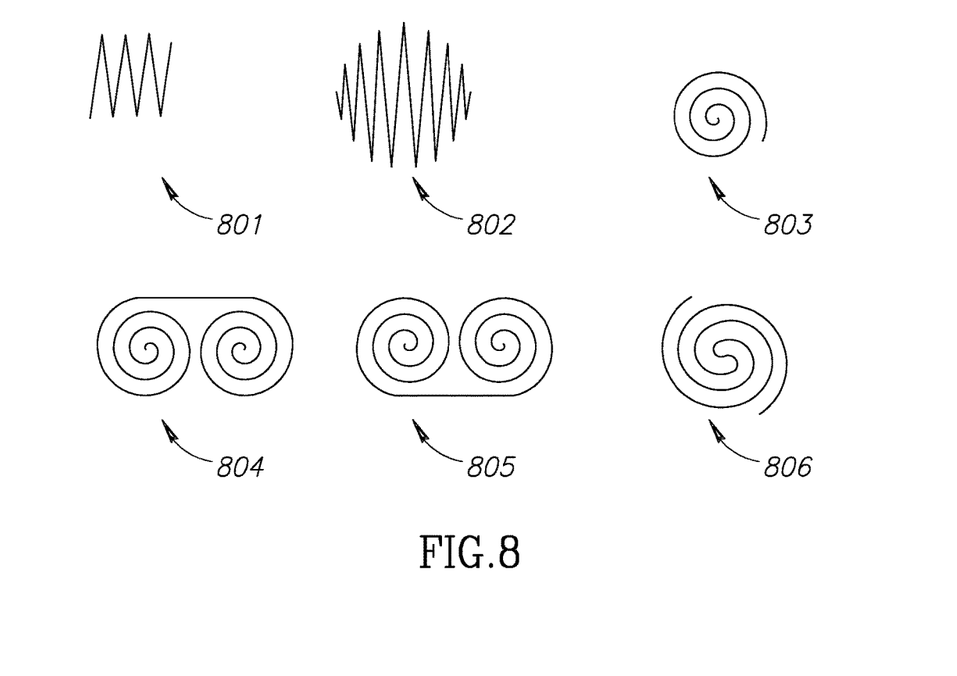
FIG. 8 shows a schematic illustration of a submandibular sling for neck lift surgery in folded mode under several configurations, according to some embodiments of the invention.

Gauzes are removed and the subcutaneous pocket is exposed from the mental incision using a retractor. The appropriate sized sling 100 is selected and folded and/or rolled into a folded mode for more convenient insertion in a small incision. Reference is now made to FIG. 8, which is a schematic illustration of a submandibular sling for neck lift surgery in folded mode under several configurations. Sling 100 may be folded to fit in a square aperture as at 801, a circular aperture as at 802, and/or the like. The folding may be performed to best allow insertion of the sling to the subcutaneous pocket from the mental or retroauricular incisions. The folding mode may be a rolled sling, such as a single roll 803, a double roll opening inferiorly 804, a double roll opening superiorly 805, a double concentric roll 806, or the like. Some patient's anatomy may be better accessed with a different folding and/or rolling pattern. Some surgical devices for insertion and expansion of the sling may be more compatible with certain folding and/or rolling patterns. Optionally, a combination of rolling and folding patterns may allow easy insertion and expansion of the sling in the subcutaneous pocket.

The rolled sling is inserted 605, such as through the medial anterior incision, and is expanded laterally until it is fully unfolded 606, with the extensions reaching towards the retroauricular incisions. Optionally, the sling may be inserted through one of the retroauricular incisions, and unfolded towards the other retroauricular incision and the mental incision with the assistance of guide threads, surgical tools, and/or the like.

One lateral hole, 104 or 105, of sling 100 is anchored 607 to the corresponding mastoid fascia with an absorbable suture. Sling 100 may be stretched from the opposite retroauricular incision with moderate tension, until a smooth look of the neck is created. During the stretching, the surgeon may spread sling 100 anteriorly from the mental incision, to keep it uniform with no ripples and/or folds. Once sling 100 is appropriately positioned, the opposite lateral holes, 105 or 104 respectively, are anchored 607 to the mastoid fascia with an absorbable suture, and finally, anterior middle holes 106 are anchored 607 to the mental fascia with absorbable sutures. Optionally, sling 100 anterior middle holes 106 are first anchored 607 to the mental fascia followed by a tensioning of each extension towards the ears and anchoring 607 the lateral holes 104 and 105.

When a patient has an excessive skin redundancy, there may be need for skin excision, such as redraping and resection 608, which are optional in this method. Incisions may be performed preauricularly to the lobule and the edge of the tragus and retroauricularly to the occipital hairline.

After attachment of sling 100, incisions may be closed 609 in two layers, and drains inserted from the retroauricular incisions for the first 24 hours. Dressings may be performed with an antibiotic ointment and gauzes, and a soft collar bandage may be worn.

Antibiotics may be prescribed for the first 7 days, such as 1-gram cephalexin three times per day. Local treatment may be performed with an antibiotic ointment. Patient may be allowed to shower after the first 24 hours, and may abstain from physical exercise on the first 4 weeks. Sutures are removed on postoperative day 7. The soft collar bandage may be worn 24/7 on the first week, then only at night for the second week.

Experimental Results

Clinical experiments were conducted to validate the device and the method described above in multiple patients who received neck lift surgical procedures with the present neck lift sling.

After surgery, incision lines were bandaged with Xeroform gauzes and pads. The head was bandaged with Kerlix™ gauze bandage rolls and a mesh.

Patients stayed overnight and drains were removed the next day.

Twenty-four hours post-surgery, the bandages were removed, the wounds cleaned with chlorhexidine, dressed with Bactroban®, and new bandages applied. The neck was supported by a cephalic support brace—a bandage loop extending below the neck, along the temples, and secured at the top of the head. If incisions were made near the patient's ears, the bandage loop covered the respective stitches and protected them. The support brace was made of an elastic foam that enables movement of the jaw and neck, while applying slight pressure for seroma prevention.

The bandages and support brace were applied for 24 hours a day, 10 days post-surgery, until the stitches were removed. Bandages were replaced twice daily, the wounds cleaned with chlorhexidine, and dressed with Bactroban®.

After 10 days, the external stitches were removed and the neck lift brace was applied 12 hours a day for an additional 10 days.

This procedure produced excellent cosmetic results, where over the course of a year following surgery, the subjects exhibited tight necks with no adverse events such as infection, folds, and discomfort. Specifically, despite the subcutaneous sling, patients reported no feeling of a foreign body in their faces.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

What is claimed is:

1. A medical method for anchoring a subcutaneous sling in neck lift surgery, comprising:
    at each ear of a patient, making incisions along a posterior edge of the tragus down through the lobule and posteriorly at the retroauricular sulcus of each said ear and through the hairline, and near a chin of the patient parallel to the mental crease line and five millimeters posterior to the crease line, wherein the incision cut near the chin has a length of 4 centimeters;
    creating a subcutaneous pocket between said incisions;
    inserting a sling into said subcutaneous pocket, wherein the sling comprises a sling body with a front edge, and two extension starting at each side of the sling and extending posteriorly and laterally from the center of the sling body;
    unfolding the sling; and
    anchoring each of the ends of the two extensions near the subcutaneous connective tissue near a corresponding ear, and the front edge of the sling to the subcutaneous tissue near the chin.

2. The medical method of claim 1, wherein the sling body and two lateral sling extensions comprise at least one bio-absorbable material.

3. The medical method of claim 1, wherein the sling body and two lateral sling extensions comprise at least one material from a group consisting of a plastic, a metal, a biological tissue, and combinations thereof.

4. The medical method of claim 1, wherein the sling body and two lateral sling extensions comprise at least one bio-absorbable plastic material from a group comprising a biodegradable plastic, biodegradable synthetic polymer, biodegradable thermoplastic polymer, biodegradable polyester, biodegradable copolymer, biocompatible plastic, and composites thereof.

5. The medical method of claim 1, wherein the sling body and two lateral sling extensions comprise at least one bio-absorbable plastic material from a group consisting of an absorbable polyglactin 910, polydioxanone, polyglycolic-acid, polylactic acid, poly(lactic-co-glycolic acid), polycaprolactone, polyglycolide, polydioxanone, and polyhydroxybutyrate.

6. The medical method of claim 1, wherein the sling body and two lateral sling extensions comprise at least one implant-grade biocompatible material from a group consisting of a polyvinyl chloride, polyethylene, polyether ether ketone, polycarbonate, polyetherimide, polysulfone, polypropylene, polyurethane, 316L stainless steel, CoCrMo, Ti6A14V, Ti6A17Nb, TiNi, and TiMo.

7. The medical method of claim 1, wherein the sling body and two lateral sling extensions comprise at least one material from a group consisting of an allograft, an isograft, a homograft, and a xenograft.

8. The medical method of claim 1, wherein the sling body and two lateral sling extensions comprise at least one material type from a group consisting of a flexible mesh, a flexible grid, a flexible plate, and a flexible sheet.

9. The medical method of claim 1, wherein the sling body and each of the two lateral sling extensions comprise an interface region between them, wherein each interface region is at least one from a group consisting of a material more flexible than the sling body, a material thinner than the sling body, and a hinge.

10. The medical method of claim 1, wherein the sling comprises at least one aperture near the middle of said narrow anterior edge and/or near a distal end of each of the two lateral sling extensions for anchoring the sling body near the chin of the patient.

* * * * *